US011471058B2

(12) United States Patent
Kang et al.

(10) Patent No.: US 11,471,058 B2
(45) Date of Patent: Oct. 18, 2022

(54) DIAGNOSTIC DEVICE, DIAGNOSTIC METHOD AND RECORDING MEDIUM FOR DIAGNOSING CORONARY ARTERY LESIONS THROUGH CORONARY ANGIOGRAPHY-BASED MACHINE LEARNING

(71) Applicants: THE ASAN FOUNDATION, Seoul (KR); UNIVERSITY OF ULSAN FOUNDATION FOR INDUSTRY COOPERATION, Ulsan (KR)

(72) Inventors: Soo Jin Kang, Seoul (KR); June Goo Lee, Seoul (KR); Hyung Joo Cho, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 21 days.

(21) Appl. No.: 16/985,928

(22) Filed: Aug. 5, 2020

(65) Prior Publication Data

US 2021/0038090 A1   Feb. 11, 2021

(30) Foreign Application Priority Data

Aug. 5, 2019   (KR) .................. 10-2019-0095169

(51) Int. Cl.
*A61B 5/02* (2006.01)
*G06T 7/11* (2017.01)
(Continued)

(52) U.S. Cl.
CPC ............ *A61B 5/02007* (2013.01); *A61B 5/06* (2013.01); *A61B 6/504* (2013.01); *G06T 7/0012* (2013.01);
(Continued)

(58) Field of Classification Search
CPC ... G06T 7/11; G06T 7/62; G06T 2207/30104; G06T 2207/20081; G06T 2207/20084;
(Continued)

(56) References Cited

U.S. PATENT DOCUMENTS

2017/0245821 A1   8/2017   Itu et al.
2021/0085397 A1*  3/2021   Passerini .............. G06N 3/0454

FOREIGN PATENT DOCUMENTS

KR   10-2018-0077140 A   7/2018

OTHER PUBLICATIONS

Hae, Hyeonyong et al., "Machine learning assessment of myocardial ischemia using angiography: Development and retrospective validation," PLOS Medicine, vol. 15, No. 11, Nov. 13, 2018 (19 pages).

(Continued)

*Primary Examiner* — Jon Chang
(74) *Attorney, Agent, or Firm* — Fitch, Even, Tabin & Flannery LLP

(57) ABSTRACT

Provided are a diagnostic device and a diagnostic method for predicting fractional flow reserve (FFR) and diagnosing coronary artery lesions via a coronary angiography-based machine learning algorithm. A deep learning-based diagnostic method for diagnosing an ischemic lesion includes: obtaining an angiography image of a patient's blood vessel; extracting a region of interest (ROI) from the angiography image; acquiring diameter information of the blood vessel in the ROI; extracting morphological features of the blood vessel based on the diameter information; and obtaining a predictive FFR value by inputting the morphological features to an artificial intelligence (AI) model and determining whether a lesion is an ischemic lesion.

5 Claims, 14 Drawing Sheets

(51) Int. Cl.
*G06T 7/62* (2017.01)
*G06T 7/00* (2017.01)
*A61B 5/06* (2006.01)
*A61B 6/00* (2006.01)

(52) U.S. Cl.
CPC .................. *G06T 7/11* (2017.01); *G06T 7/62* (2017.01); *G06T 2207/20081* (2013.01); *G06T 2207/20084* (2013.01); *G06T 2207/20104* (2013.01); *G06T 2207/30096* (2013.01); *G06T 2207/30101* (2013.01); *G06T 2207/30104* (2013.01)

(58) Field of Classification Search
CPC . G06T 2207/20104; G06T 2207/30096; G06T 7/0012; G06T 5/20; G06T 2207/10116; G06T 2207/30101; A61B 5/02007; A61B 5/06; A61B 6/5217; A61B 6/469; A61B 6/504; G16H 50/20; G16H 30/40; G06N 3/08; G06N 3/0454; G06N 3/0427
See application file for complete search history.

(56) References Cited

OTHER PUBLICATIONS

Cho, Hyungjoo et al., "Angiography-Based Machine Learning for Predicting Fractional Flow Reserve in Intermediate Coronary Artery Lesions," Journal of the American Heart Association, Feb. 19, 2019 (18 pages).

* cited by examiner

FIG. 4

| | Training Set | Test Set |
|---|---|---|
| Number of patients/lesions | 1204/1204 | 297/297 |
| Age, y | 62.6 ±9.7 | 62.1 ±10.0 |
| Men | 929 (77) | 228 (77) |
| Diabetes mellitus | 393 (31) | 89 (30) |
| Hypertension | 783 (65) | 198 (67) |
| Current smoker | 493 (43) | 134 (45) |
| Hyperlipidemia | 394 (66) | 193 (65) |
| Stable (vs unstable) angina | 987 (82) | 252 (85) |
| Body surface area, $m^2$ | 1.74 ±.16 | 1.74 ±.16 |
| FFR at maximal hyperemia | 0.79 ±.10 | 0.79 ±.10 |
| Involved segment | | |
| Proximal LAD | 509 (42) | 115 (39) |
| Mid LAD | 293 (24) | 89 (29) |
| Distal LAD | 11 (1) | 0 (0) |
| Proximal LCX | 67 (6) | 20 (7) |
| Distal LCX | 55 (5) | 13 (4) |
| Proximal RCA | 145 (12) | 33 (11) |
| Mid RCA | 90 (8) | 20 (7) |
| Distal RCA | 34 (3) | 7 (2) |

FIG. 8

| Feature | Definition |
|---|---|
| Maximal lumen diameter, mm | Maximal lumen diameter within the ROI (points A~K) |
| MLD, mm | Minimal lumen diameter within the ROI (points A~K) |
| Proximal lumen diameter, mm | Mean lumen diameter between the ostium and the proximal edge (points A~E) |
| Distal lumen diameter, mm | Mean lumen diameter between the distal edge and the end of ROI (points H~K) |
| Proximal 5-mm RLD, mm | Mean lumen diameter within the proximal 5-mm reference |
| Distal 5-mm RLD, mm | Mean lumen diameter within the distal 5-mm reference |
| Averaged RLD, mm | Average of proximal and distal 5-mm RLDs |
| Lumen diameter within the worst segment, mm | Mean lumen diameter within the worst segment (points F and G) |
| DS, % | [Averaged RLD-MLD]/Averaged RLD x 100 |
| Distance to MLD, mm | Distance from the ostium to the MLD (point A~MLD) |
| Length of the proximal reference, mm | Length of the proximal reference (points C~E) |
| Distance to the distal reference, mm | Distance from the ostium to the distal reference (points A~J) |
| Lesion length, mm | Length of the lesion (points E~H) |
| Length-D <2.0, mm | Total length of the segment with lumen diameter <2.0 mm |
| Length-D <1.75, mm | Total length of the segment with lumen diameter <1.75 mm |
| Length-D <1.5, mm | Total length of the segment with lumen diameter <1.5 mm |
| Length-D <1.25, mm | Total length of the segment with lumen diameter <1.25 mm |
| Length-D <1.0, mm | Total length of the segment with lumen diameter<1.0 mm |
| Length-DS >25, mm | Total length of the segment with DS >25% |
| Length-DS >50, mm | Total length of the segment with DS >50% |
| Length-DS >70, mm | Total length of the segment with DS >70% |
| Longitudinal eccentricity | Ratio of the length of point E~MLD to the lesion length |
| Proximal slope | [Lumen diameter at the proximal edge-MLD]/length of point E~MLD |
| Distal slope | [Lumen diameter at the distal edge-MLD]/length of MLD~point H |
| Segment | Involved segment |
| Body surface area | Body surface area |
| Sex | Male or female |
| Age | Years of age |

FIG. 10

| | AUC | Sensitivity | Specificity | PPV | NPV | Overall Accuracy |
|---|---|---|---|---|---|---|
| Using all 28 features | | | | | | |
| Training set (5-fold CV)* | 0.84±.03 | 0.78±.04 | 0.78±.05 | 0.77±.05 | 0.79±.05 | 0.78±.04 |
| Test set | 0.86 | 0.82 | 0.79 | 0.79 | 0.82 | 0.80 |
| External validation cohort | 0.90 | 0.72 | 0.89 | 0.75 | 0.87 | 0.84 |
| Using the 12 selected features | | | | | | |
| Training set | 0.86 | 0.79 | 0.80 | 0.77 | 0.82 | 0.79 |
| Test set | 0.87 | 0.84 | 0.80 | 0.81 | 0.84 | 0.82 |
| External validation cohort | 0.87 | 0.80 | 0.87 | 0.74 | 0.90 | 0.85 |
| By 2000 bootstrap iterations | | | | | | |
| Training set† | 0.87±.01 (0.86-0.88) | 0.81±.01 (0.79-0.83) | 0.77±.01 (0.74-0.79) | 0.75±.01 (0.73-0.76) | 0.83±.01 (0.81-0.84) | 0.79±.01 (0.77-0.80) |
| Test set† | 0.87±.01 (0.86-0.88) | 0.84±.02 (0.81-0.87) | 0.77±.01 (0.75-0.80) | 0.78±.01 (0.76-0.80) | 0.83±.01 (0.81-0.86) | 0.81±.01 (0.79-0.82) |

DIAGNOSTIC DEVICE, DIAGNOSTIC METHOD AND RECORDING MEDIUM FOR DIAGNOSING CORONARY ARTERY LESIONS THROUGH CORONARY ANGIOGRAPHY-BASED MACHINE LEARNING

CROSS-REFERENCE TO RELATED APPLICATION

This application claims the benefit of Korean Patent Application No. 10-2019-0095169, filed on Aug. 5, 2019, in the Korean Intellectual Property Office, the disclosure of which is incorporated herein in its entirety by reference.

BACKGROUND

1. Field

One or more embodiments relate to an artificial intelligence (AI) system and an application thereof for simulating functions of a human brain such as cognition and decision-making by using machine learning algorithms, and more particularly, to a diagnostic device, a diagnostic method, and a recording medium for predicting fractional flow reserve (FFR) and detecting coronary artery lesions via a coronary angiography-based machine learning algorithm.

2. Description of Related Art

Recently, artificial intelligence (AI) systems that simulate human-level intelligence have been used in various fields. An AI system enables machines to become smart by learning and making decisions on their own, compared to an existing rule-based smart system. The AI system may improve its recognition rates and is capable of understanding a user's preferences more accurately through experience. Thus, existing rule-based smart systems are increasingly being replaced by deep learning-based AI systems. AI technology consists of machine learning (e.g., deep learning) and element technologies using the machine learning.

Intravascular ultrasound (IVUS) is a clinical examination method used to recognize morphological features of coronary artery lesions, observe coronary atherosclerosis, and optimize stent implantation. However, an IVUS technique of the related art has a limitation in that it cannot determine the necessity of a procedure due to the difficulty in identifying the presence or absence of ischemia in a stenotic lesion.

In particular, to evaluate the presence of ischemia in a coronary lesion with intermediate stenosis, an FFR measurement needs to be repeatedly performed during a procedure. In other words, it is necessary to determine whether myocardial ischemia occurs through an FFR for making decisions with respect to treatment of a coronary lesion with stenosis. However, an FFR test is considered expensive (about KRW 1,000,000), requires a long test time, and has a risk of complications associated with the administration of adenosine.

To solve these problems, attention has recently been focused on an instantaneous wave-free ratio (iFR) technique capable of predicting an FFR with 80% accuracy even without using adenosine, but the iFR technique is not effective in reducing the cost because it requires the use of an expensive blood flow pressure wire like the FFR technique. For another approach, a quantitative flow ratio (QFR) has recently been known as an angiocardiography-based technique for predicting an FFR with 80% to 85% accuracy. However, this approach is significantly time consuming because an FFR may be calculated only based on 3D reconstruction from two different matching images and has a low feasibility due to the relative difficulty of obtaining an appropriate image.

Guidelines have recommended detection of an ischemic lesion via an FFR test before the procedure, but in more than 70% of all procedures, decisions on whether to perform the procedures are actually made only based on a shape of stenosis on an angiographic or IVUS image due to the cost and time. Due to this, unnecessary stent procedures are being abused, and a solution for preventing such abuse of stenting is required.

SUMMARY

One or more embodiments include a device, method, and a recording medium used to acquire pieces of morphological information associated with a fractional flow reserve (FFR) of less than 0.80 based on coronary angiography and diagnose ischemia without performing an FFR technique via machine learning based on the pieces of morphological information.

However, these objectives are merely an example, and the scope of the present disclosure is not limited thereto.

Additional aspects will be set forth in part in the description which follows and, in part, will be apparent from the description, or may be learned by practice of the presented embodiments of the disclosure.

According to one or more embodiments, a diagnostic method performed by a device for diagnosing an ischemic lesion in a blood vessel includes: obtaining an angiography image of a patient's blood vessel; extracting a region of interest (ROI) from the angiography image; acquiring diameter information of the blood vessel in the ROI; extracting morphological features of the blood vessel based on the diameter information; and obtaining a predictive FFR value by inputting the morphological features to an artificial intelligence (AI) model and determining whether a lesion is an ischemic lesion.

The diagnostic method may further include obtaining clinical features of the patient, and the determining of whether the lesion is an ischemic lesion may include obtaining the predictive FFR value by inputting the morphological features and the clinical features to the AI model and determining whether the lesion is an ischemic lesion.

The ROI may be a region of the blood vessel from an ostium that is an entrance to the blood vessel to a distal reference that is a preset distance from a lesion included in the blood vessel, and the extracting of the ROI may include: detecting a location of the lesion in the blood vessel; and automatically extracting the ROI based on the location of the lesion.

The acquiring of the diameter information may include: obtaining a centerline of the blood vessel included in the ROI; and acquiring the diameter information based on a virtual line perpendicular to the centerline.

According to one or more embodiments, a computer-readable recording medium has recorded thereon a program for executing an ischemic lesion diagnostic method.

According to one or more embodiments, a device for diagnosing an ischemic lesion in a blood vessel includes: an image acquirer configured to obtain an angiography image of a patient's blood vessel; an ROI extractor configured to extract an ROI from the angiography image; a diameter information acquirer configured to acquire diameter information of the blood vessel in the ROI; a feature extractor configured to extract morphological features of the blood vessel based on the diameter information; and an ischemic lesion diagnoser configured to obtain a predictive FFR value by inputting the morphological features to an AI model and determine whether a lesion is an ischemic lesion.

Additional aspects, features, and advantages other than described above will become apparent from the detailed description, claims, and drawings for implementing the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4 is table illustrating a training set, a test set, and baseline characteristics for training an artificial intelligence (AI) model, according to an embodiment of the disclosure;

FIG. 8 is a table illustrating feature information acquired by an ischemic lesion diagnostic device, according to an embodiment of the disclosure;

FIG. 10 illustrates the performance of an AI model trained by performing 5-fold cross validation on a training set and a test set, respectively, according to an embodiment of the disclosure;

DETAILED DESCRIPTION

Figure 1:
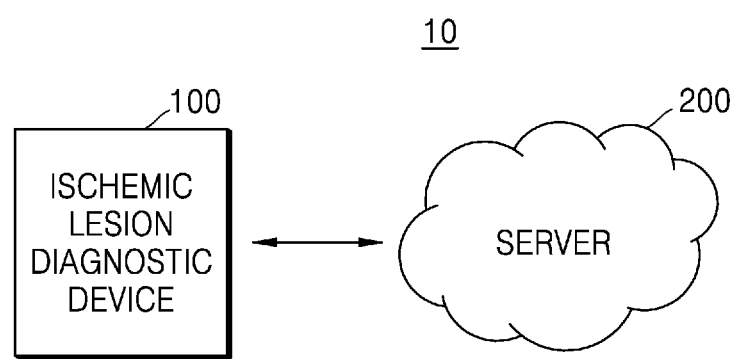
FIG. 1 is a system diagram illustrating an ischemic lesion diagnostic system according to an embodiment of the disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, various embodiments of the present disclosure will be described with reference to the accompanying drawings. The present disclosure may have various modifications and embodiments and thus will be described in detail with respect to particular embodiments illustrated in the drawings. However, it should be understood that the embodiments are not intended to limit the scope of the present disclosure; rather, the present disclosure should be construed to cover all modifications, equivalents, and/or alternatives falling within the spirit and scope of the embodiments of the disclosure. In connection with descriptions of the drawings, like reference numerals denote like elements.

In various embodiments of the present disclosure, the expression "include (comprise)" or "may include (comprise)" refers to the presence of a corresponding function, operation, or element presented herein, and does not limit the presence of one or more additional functions, operations, or elements. Furthermore, throughout the present specification, the terms such as "include (comprise)" and/or "have" may be construed to indicate the presence of characteristics, numbers, steps, operations, components, elements, or combinations thereof, but may not be construed to exclude the presence or addition of one or more other characteristics, numbers, steps, operations, components, elements, or combinations thereof.

In the present disclosure, the term "or" includes any or all combinations of words enumerated together. For example, the expression "A or B" may include only A, only B, or both A and B.

The terms "first", "second", etc. used herein may modify various elements in various embodiments, but may not limit such elements. For example, these terms do not limit the order and/or importance of the elements. The terms may be used merely for distinguishing an element from another element. For example, a first user device and a second user device both indicate different user devices although both of them are user devices. For example, a first element could be termed a second element, and similarly, a second element could be also termed a first element without departing from the scope of the present disclosure.

Throughout the specification, it will be understood that when an element is referred to as being "connected" or "coupled" to another element, the element may be directly connected to or electrically coupled to the other element with one or more intervening elements interposed therebetween. On the other hand, when an element is referred to as being "directly connected" or "directly coupled" to another element, it should be understood that no element is interposed therebetween.

Terms such as "module", "unit", "part", etc. used herein indicate an element for performing one or more functions or operations, and the element may be embodied as hardware or software or a combination of hardware and software. Furthermore, a plurality of "modules", "units", or "parts" may be integrated into at least one module or chip and implemented as at least one processor, except for a case where the respective "modules", "units", or "parts" need to be implemented as discrete particular hardware.

Hereinafter, various embodiments of the disclosure will be described in greater detail with reference to the accompanying drawings.

FIG. 1 is a system diagram illustrating an ischemic lesion diagnostic system 10 according to an embodiment of the disclosure.

Referring to FIG. 1, the ischemic lesion diagnostic system 10 of the present disclosure may include an ischemic lesion diagnostic device 100 and a server 200.

The ischemic lesion diagnostic device 100 is a device for predicting and diagnosing an ischemic lesion occurring in a patient's coronary artery.

Whether a lesion in the coronary artery is an ischemic lesion is determined not based on an appearance of stenosis in the coronary artery lesion but based on functional severity of coronary artery stenosis. In other words, even when there is a stenosis in the lesion by appearance, the lesion may not be determined as an ischemic lesion. Fractional flow reserve (FFR) is defined as the ratio of maximal coronary blood flow in an artery with stenosis to maximal coronary blood flow in the same artery without stenosis. Thus, whether the lesion is an ischemic lesion caused by functional stenosis may be determined through FFR.

Accordingly, the ischemic lesion diagnostic device 100 may determine whether the lesion is an ischemic lesion by predicting an FFR value of the coronary artery. In detail, an FFR of 0.8 indicates that a stenotic coronary artery supplies 80% of the normal maximal flow, and the ischemic lesion diagnostic device 100 may determine a lesion with an FFR of 0.80 or less as being an ischemic lesion with functional stenosis in the coronary artery.

The server 200 is at least one external server for training and updating an AI model and performing prediction via the AI model.

According to an embodiment of the disclosure, the server 200 may include an AI model for predicting an FFR in a blood vessel based on morphological features of the blood vessel included in a coronary angiography image and clinical features of a patient.

In this case, when various pieces of feature information regarding the morphological features of the blood vessel, the clinical features, etc. are input to the AI model, the AI model may determine whether or not an FFR value for a coronary artery lesion is 0.80 or less. In this case, the feature information may include morphological features, computational features, and clinical features of a patient on an angiographic image, but is not limited thereto.

Although FIG. 1 shows that the ischemic lesion diagnostic device 100 and the server 200 are implemented as separate components, according to an embodiment of the disclosure, they may be implemented as a single component. In other words, according to an embodiment, the ischemic lesion diagnostic device 100 may be an on-device AI apparatus for directly training and refining an AI model. Hereinafter, it is assumed that the ischemic lesion diagnostic device 100 is an on-device AI apparatus including an AI model.

Figure 2:
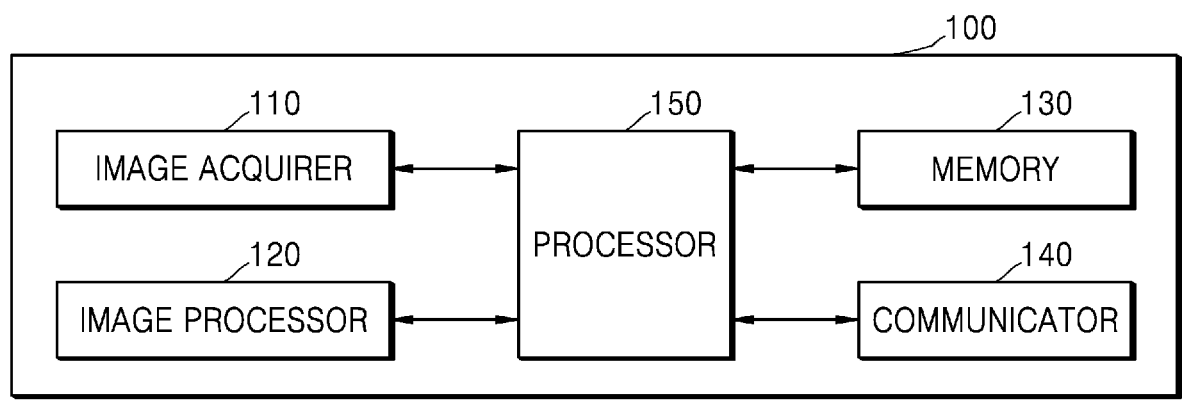
FIG. 2 is a simplified block diagram for describing components of an ischemic lesion diagnostic device according to an embodiment of the disclosure.

FIG. 2 is a simplified block diagram for describing components of an ischemic lesion diagnostic device according to an embodiment of the disclosure.

Referring to FIG. 2, the ischemic lesion diagnostic device 100 may include an image acquirer 110, an image processor 120, a memory 130, a communicator 140, and a processor 150 that is electrically connected to and controls the above-described components.

The image acquirer 110 may acquire angiography image data via various sources. For example, after administration of 250 g of nitroglycerine in a coronary artery, the image acquirer 110 may obtain an angiography image by inserting a 5F or 7F catheter into a radial artery or femoral artery. Image data acquired by the image acquirer 110 may be processed by the image processor 120.

The image processor 120 may process the image data acquired via the image acquirer 110. The image processor 120 may perform various image processing methods on the image data, such as decoding, scaling, noise filtering, frame rate conversion, or resolution conversion.

The memory 130 may store various pieces of data for all operations of the ischemic lesion diagnostic device 100, such as a program for processing or control by the processor 150. The memory 130 may store a plurality of application programs or applications driven by the ischemic lesion diagnostic device 100, as well as data and instructions for operations of the ischemic lesion diagnostic device 100. At least some of these application programs may be downloaded from an external server via wireless communication.

Furthermore, at least some of these application programs may exist on the ischemic lesion diagnostic device 100 at the time of manufacture for basic functions of the ischemic lesion diagnostic device 100. The application programs may be stored in the memory 130 and driven by the processor 150 to perform operations (or functions) of the ischemic lesion diagnostic device 100. In particular, the memory 130 may be implemented as an internal memory such as read-only memory (ROM) or random access memory (RAM) included in the processor 150, or may be implemented as a memory separate from the processor 150.

The communicator 140 may be a component that communicates with various types of external devices according to various types of communication methods. The communicator 140 may include at least one of a Wi-Fi chip, a Bluetooth chip, a wireless communication chip, and a near field communication (NFC) chip. The processor 150 may communicate with the server 200 or various external devices via the communicator 140.

In particular, when using the Wi-Fi chip or Bluetooth chip, the processor 150 may first transmit or receive various types of connection information such as an SSID and a session key and then various types of information after establishing a communication connection by using the connection information. The wireless communication chip refers to a chip for performing communication according to various communication standards such as IEEE, Zigbee, 3rd Generation (3G), 3G Partnership Project (3GPP), and Long Term Evolution (LTE). The NFC chip refers to a chip that operates according to an NFC method using a 13.56 MHz band among various radio frequency identification (RF-ID) frequency bands such as 135 kHz, 13.56 MHz, 433 MHz, 860 to 960 MHz, and 2.45 GHz.

The processor 150 is a component for controlling all operations of the ischemic lesion diagnostic device 100. In detail, the processor 150 controls all operations of the ischemic lesion diagnostic device 100 by using various programs stored in the memory 130 of the ischemic lesion diagnostic device 100. For example, the processor 150 may include a central processing unit (CPU), RAM, ROM, and a system bus. The ROM is a component in which an instruction set for booting the system is stored, and the CPU copies an operating system (OS) stored in the memory 130 of the ischemic lesion diagnostic device 100 to the RAM and executes the OS to boot the system according to instructions stored in the ROM. When booting is completed, the CPU may copy various applications stored in the memory 130 to the RAM and execute the applications to perform various operations. While it has been described that the processor 150 includes only one CPU, the processor 150 may be implemented with a plurality of CPUs (or digital signal processors (DSPs), a system on chip (SoC), etc.).

According to an embodiment of the disclosure, the processor 150 may be implemented as a microprocessor, a time controller (TCON), or a DSP for processing digital signals. However, embodiments of the disclosure are not limited thereto, the processor 150 may include one or more of a CPU, a micro controller unit (MCU), a micro processor unit (MPU), a controller, an application processor (AP), a communication processor (CP), and an ARM processor or may be defined as a corresponding term. Furthermore, the processor 150 may be implemented as an SoC or large scale integration (LSI) having a processing algorithm built therein or in the form of a field programmable gate array (FPGA).

Figure 3:
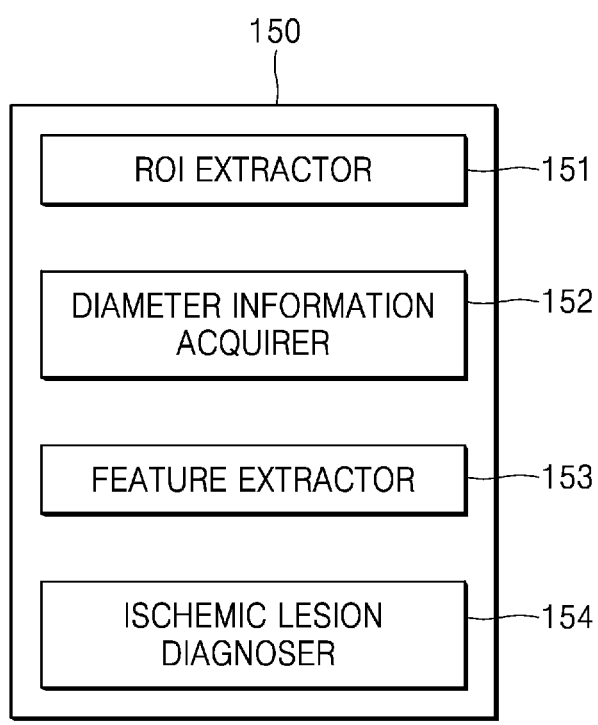
FIG. 3 is a simplified block diagram for describing components of a processor according to an embodiment of the disclosure.

FIG. 3 is a simplified block diagram for describing components of the processor 150 according to an embodiment of the disclosure.

According to an embodiment of the disclosure, the processor 150 may include a region of interest (ROI) extractor 151, a diameter information acquirer 152, a feature extractor 153, and an ischemic lesion diagnoser 154.

The ROI extractor 151 is a component for extracting an ROI from an angiography image. In this case, the ROI may be a region of a blood vessel from an ostium of the blood vessel to a distal reference that is a preset distance (e.g., 10 mm) from a lesion included in the blood vessel, but is not limited thereto.

In detail, the ROI extractor 151 may subdivide the ROI into the ostium that is an entrance to the blood vessel, a proximal reference, a lesion, and the distal reference by using an edge detection software (e. g., CAAS-5; Pie-Medical).

The diameter information acquirer 152 is a component for acquiring diameter information of the blood vessel. In this case, the diameter information acquirer 152 may extract a centerline of the blood vessel included in the ROI and acquire diameter information by using a virtual line perpendicular to the centerline.

In detail, the diameter information acquirer 152 may convert a distance between the ostium of the blood vessel and the distal reference that is a preset distance (e.g., 10 mm) away from the lesion included in the blood vessel into a velocity function and extract an optimal path as the centerline by using a fast marching algorithm (FMA). In this case, the centerline may be sampled at equal intervals by smoothing the centerline via convolution using a Gaussian kernel function.

The diameter information acquirer 152 may then find an end position of a lumen area by using two lines that are perpendicular to the centerline at each point on the centerline and obtain a distance between two end points as a lumen diameter. Moreover, according to an embodiment of the disclosure, the diameter information acquirer 152 may calibrate the lumen diameter by multiplying a scale factor calculated as a caliber of a guiding catheter divided by a pixel distance between two edges of the guiding catheter. In this case, a series of lumen diameters along the centerline may be plotted via filtering (e.g., median filtering).

The feature extractor 153 may extract morphological features of the blood vessel based on the diameter information acquired by the diameter information acquirer 152. For example, the feature extractor 153 may extract morphological features such as a digital lumen diameter (mm), a minimal lumen diameter (MLD, mm) within the ROI, and a total length of a segment with a lumen diameter of 1.5 mm or less (Length-D<1.5, mm).

The ischemic lesion diagnoser 154 may predict an FFR value based on the morphological features extracted by the feature extractor 153 and clinical features of a patient and determine whether the lesion is an ischemic lesion based on the predicted FFR value.

Moreover, the ischemic lesion diagnoser 154 may include an AI model that outputs whether an FFR value for the coronary artery lesion is 0.80 or less when various pieces of feature information regarding the morphological features of the blood vessel, the clinical features, etc. are input to the AI model. In this case, the feature information may include morphological features, computational features, and clinical features of a patient on an angiographic image, but is not limited thereto.

FIG. 4 is a table illustrating a training set, a test set, and baseline characteristics for training an AI model, according to an embodiment of the disclosure.

From 2010 to 2015, evaluations were performed on 1717 patients who underwent coronary angiography and FFR measurement. When FFR was measured in several lesions, a patient having a primary coronary artery lesion with the lowest FFR value was selected. In this case, 1,501 images were used as a final cohort, excluding images of patients with poor quality or technical errors in an image file.

Regarding acquisition of a patient's FFR, "equalizing" was performed with a guidewire sensor located at a tip of a guide catheter, and a 0.014-inch FFR pressure guidewire was advanced distal to a stenosis. FFR was measured at maximal hyperemia induced by intravenous infusion of adenosine. In other words, in order to improve detection of hemodynamically significant stenosis, a dose of adenosine administered via a central vein at 140 μg/kg/min was increased to 200 μg/kg/min. After performing hyperemic pressure recording, FFR was obtained as a ratio of a distal coronary pressure to a normal perfusion pressure (aortic pressure) at maximal hyperemia.

The patients were assigned to a training set and the test set, respectively, at a 4:1 ratio. In other words, information of 1,204 patients was used as a training set for training the AI model while information of non-overlapping 297 patients was used to evaluate the performance of the AI model.

The baseline characteristics may include clinical features of a patient and an involved segment. In this case, the clinical features of the patient may include age, gender (men), smoking (current smoker), body surface area, FFR at maximal hyperemia, etc. The involved segment may be a portion of a coronary artery where a stenotic lesion occurs and include left anterior descending artery (LAD), left circumflex artery (LCX), and right coronary artery (RCA).

Figure 5A:
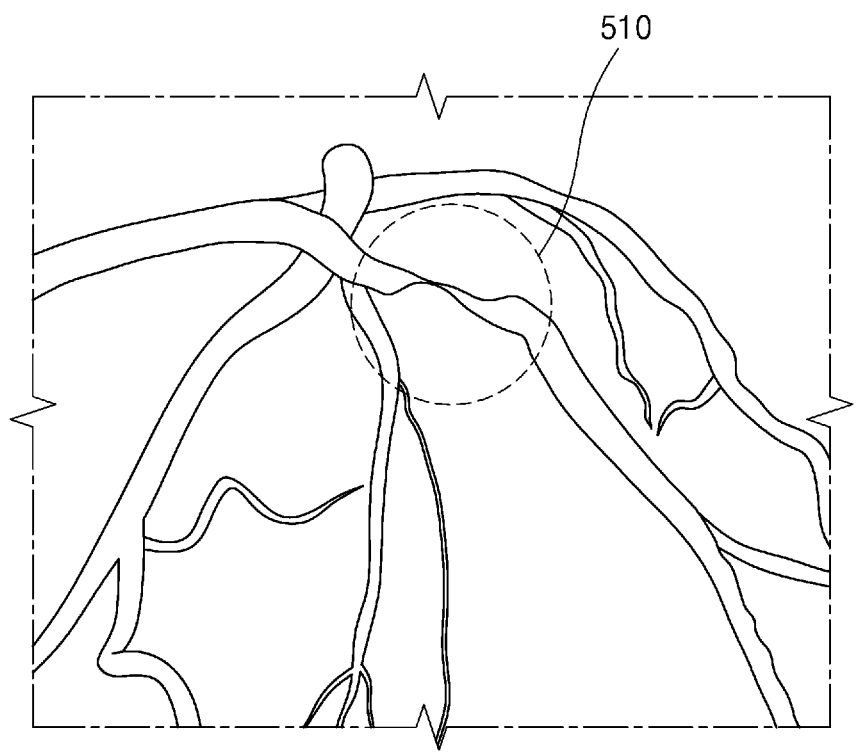
FIGS. 5A through 5C are diagrams for describing lesion detection, blood vessel segmentation, and centerline extraction according to an embodiment of the disclosure.
Figure 5B:
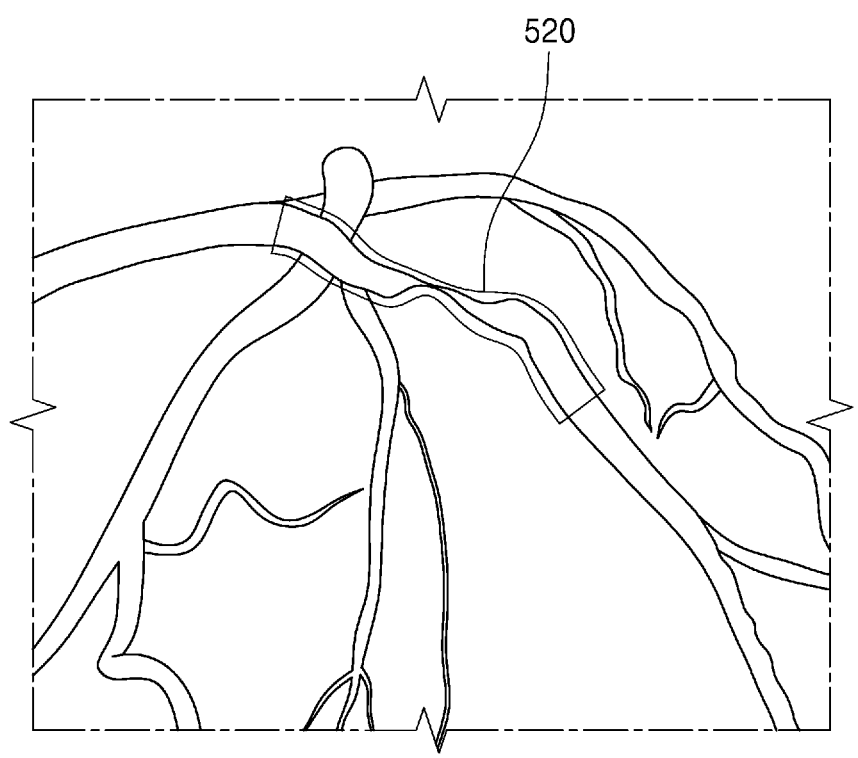
Figure 5C:
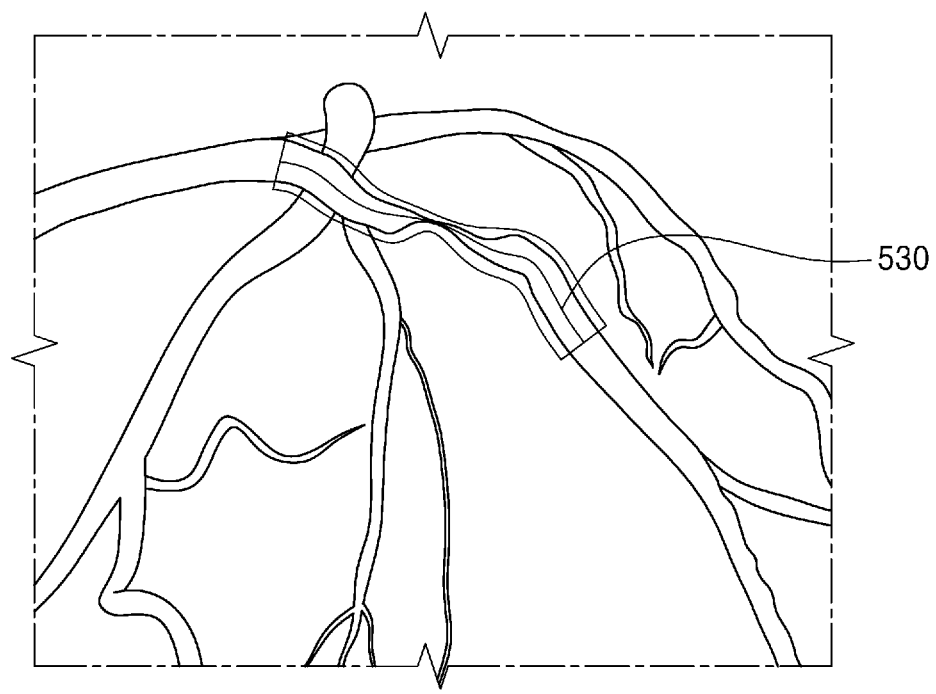

FIGS. 5A through 5C are diagrams for describing lesion detection, blood vessel segmentation, and centerline extraction according to an embodiment of the disclosure.

Referring to FIG. 5A, the ischemic lesion diagnostic device 100 may extract a lesion 510 from an angiography image. The ischemic lesion diagnostic device 100 may determine, as a lesion, a portion of a blood vessel in which stenosis seemingly occurs due to narrowing compared to other portions of the blood vessel when seen with the naked eye. As seen on FIG. 5A, stenosis seemingly occurs in the lesion 510 compared to other portions of the blood vessel.

Referring to FIG. 5B, the ischemic lesion diagnostic device 100 may extract an ROI 520 from an angiography image. The ischemic lesion diagnostic device 100 may set the ROI 520 around a portion determined as the lesion 510. The ischemic lesion diagnostic device 100 may subdivide the ROI around the lesion 510 into an ostium that is an entrance to the blood vessel, a proximal reference, a lesion, and a distal reference by using the edge detection software (e. g., CAAS-5; Pie-Medical).

In this case, the ROI 520 may be a region of a blood vessel from the ostium of the blood vessel to the distal reference that is a preset distance (e.g., 10 mm) from the lesion included in the blood vessel, but is not limited thereto.

Thereafter, referring to FIG. 5C, the ischemic lesion diagnostic device 100 may extract a centerline 530 of the blood vessel from the ROI 520 in an angiography image. As described above, the ischemic lesion diagnostic device 100 may convert a distance between the ostium of the blood vessel and the distal reference that is a preset distance (e.g., 10 mm) away from the lesion 510 included in the blood vessel into a velocity function and extract an optimal path as the centerline 530 by using an FMA. Thereafter, diameter information may be obtained using a virtual line perpendicular to the centerline 530.

Figure 6:
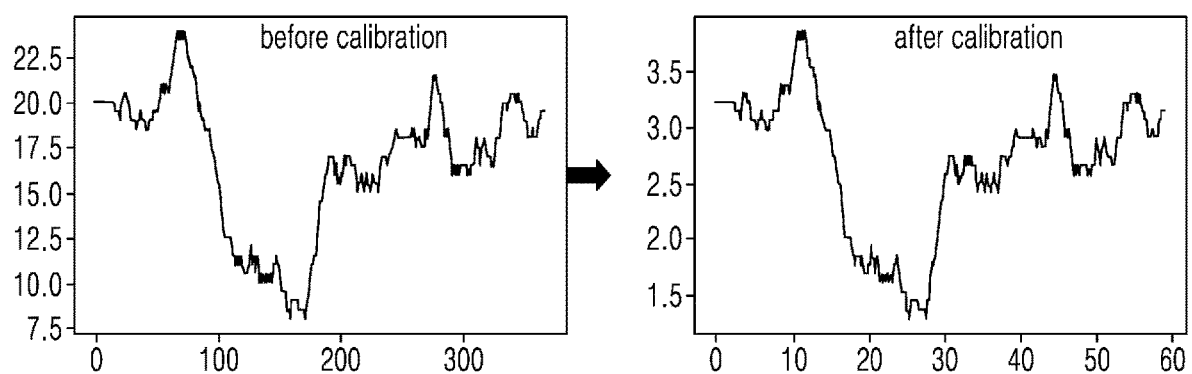
FIG. 6 illustrates calibration of a lumen diameter according to an embodiment of the disclosure.

FIG. 6 illustrates calibration of a lumen diameter according to an embodiment of the disclosure.

Referring to 6, the ischemic lesion diagnostic device 100 may measure a lumen diameter using two lines that are perpendicular to an extracted centerline at each point on the centerline, and measured lumen diameters at points on the centerline may be plotted via convolution.

Moreover, the ischemic lesion diagnostic device 100 may calibrate the plotted lumen diameters by using a scale factor. In this case, the scale factor may be calculated using a known caliber (mm) of a guiding catheter. In other words, the scale factor may be calculated by estimating a length per pixel based on a pixel distance between two edges of the guiding catheter.

The lumen diameters estimated based on the centerline may be calibrated by multiplying the calculated scale factor by the lumen diameters, and the calibrated lumen diameters may then be plotted.

Figure 7:
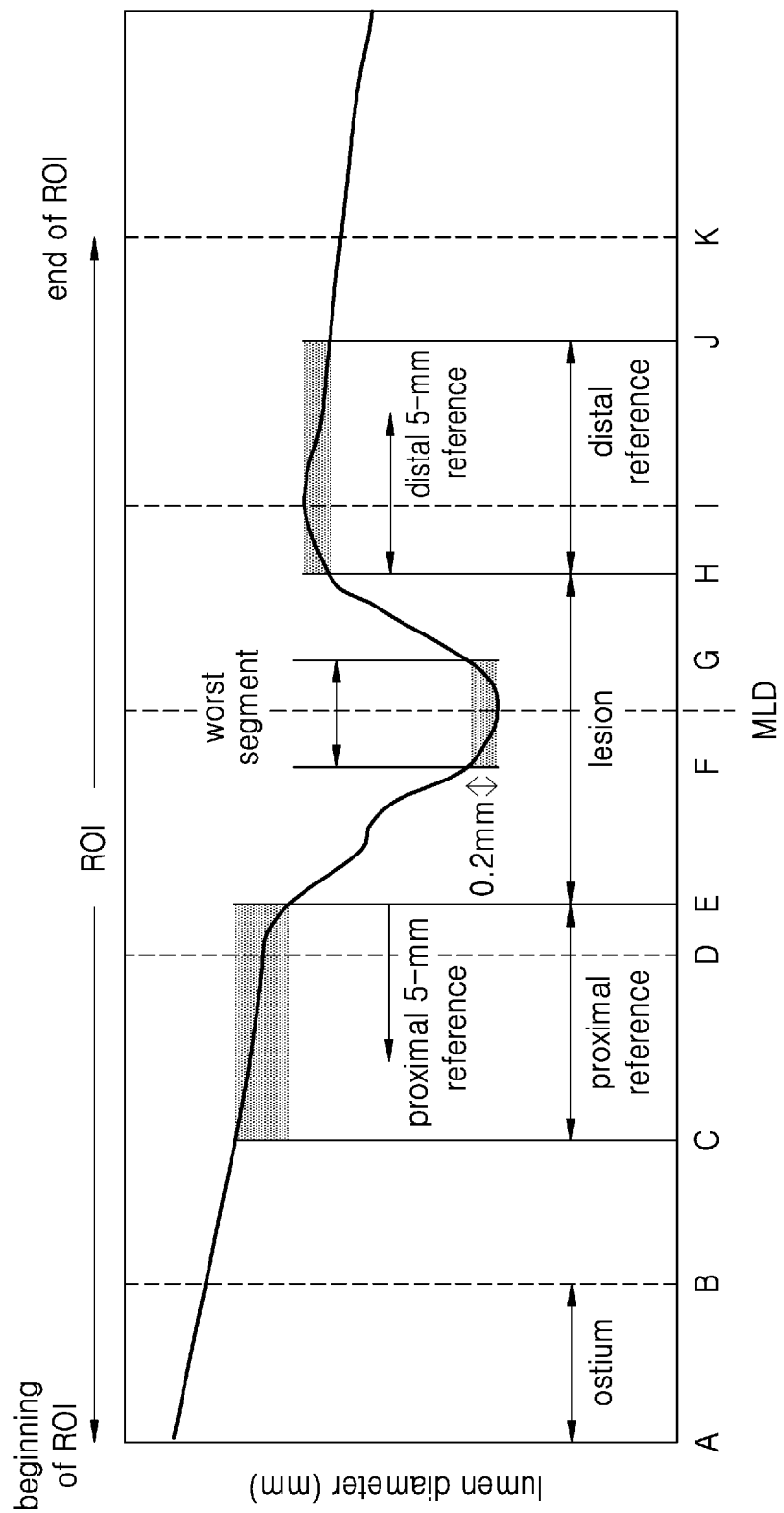
FIG. 7 is a diagram for describing morphological segmentation of a blood vessel with respect to a lumen diameter and a position in the blood vessel, according to an embodiment of the disclosure.

FIG. 7 is a diagram for describing morphological segmentation of a blood vessel with respect to a lumen diameter and a position in the blood vessel, according to an embodiment of the disclosure;

Referring to FIG. 7, a region corresponding to points A to K is an ROI of a blood vessel. The ROI may be a region including an ostium of the blood vessel to a distal reference.

In this case, the ostium of the blood vessel may be a segment corresponding to points A to B, and the distal reference may be a segment (points H to J) that is a certain distance (e.g., 10 mm) from a segment determined as a lesion (points E to H) of the blood vessel.

A proximal reference may be a segment (points C to E) that is a certain distance (e.g., 10 mm) from the segment determined as the lesion (points E to H) of a blood toward the ostium. The ischemic lesion diagnostic device 100 may determine a portion of the lesion having the smallest lumen diameter as a worst segment (points F to G).

The ischemic lesion diagnostic device 100 may extract morphological features of a blood vessel based on a lumen diameter plot as shown in FIG. 7. Features extracted by the ischemic lesion diagnostic device 100 will now be described in detail with reference to FIG. 8.

FIG. 8 is table showing feature information acquired by the ischemic lesion diagnostic device 100, according to an embodiment of the disclosure.

Referring to FIG. 8, the ischemic lesion diagnostic device 100 may obtain clinical features of a patient and morphological features of a blood vessel.

In this case, the clinical features may include age, gender, a body surface area, and an involved segment. However, this is merely an example, and the clinical features may include involvement of proximal LAD and a vessel type.

The morphological features of a blood vessel may include maximal lumen diameter, MLD, proximal lumen diameter, distal lumen diameter, proximal 5-mm reference lumen diameter (RLD), distal 5-mm RLD, averaged RLD, lumen diameter within the worst segment, diameter stenosis (DS), distance to MLD, length of the proximal reference, distance to the distal reference, lesion length, length-D<2.0, length-D<1.75, Length-D<1.5, length-D<1.25, length-D<1.0, length-DS>25, length-DS>50, proximal slope, distal slope, etc.

Figure 9:
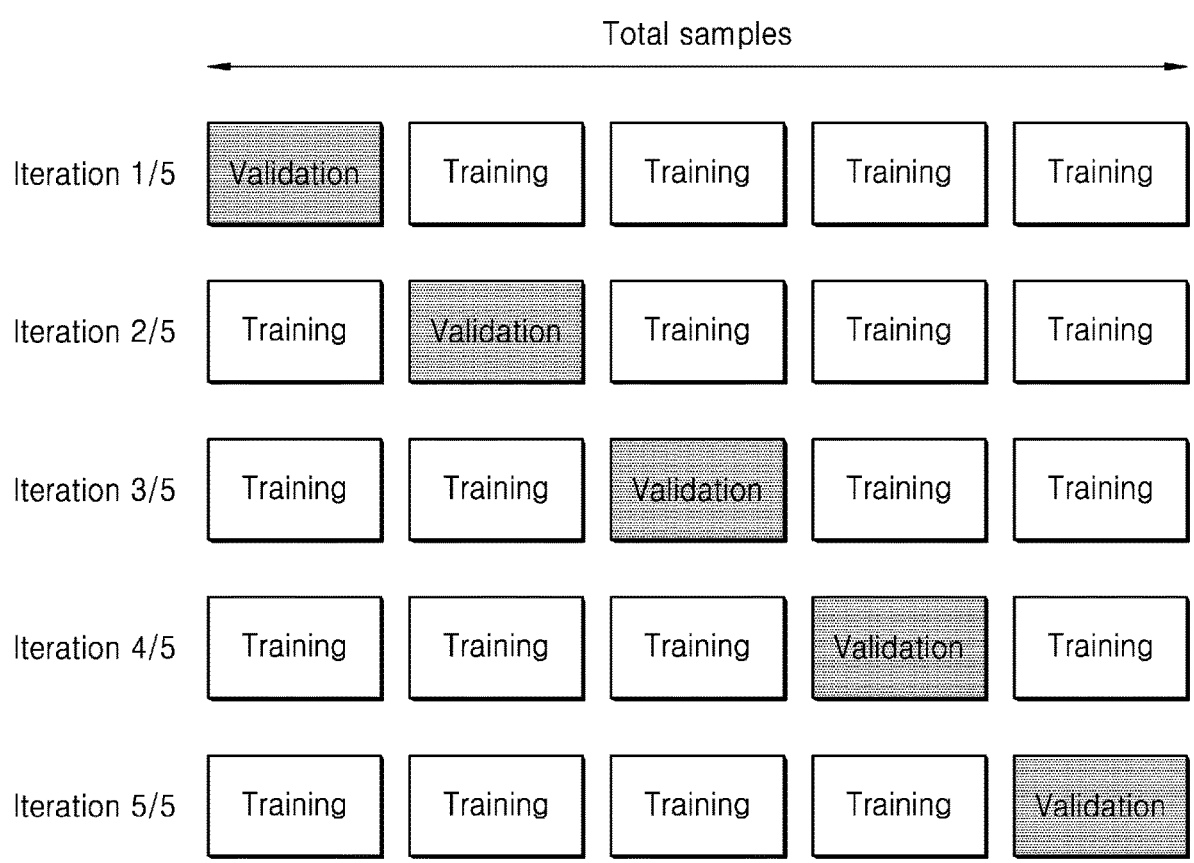
FIG. 9 illustrates training and validation through 5-fold cross validation, according to an embodiment of the disclosure.

FIG. 9 illustrates training and validation through 5-fold cross validation, according to an embodiment of the disclosure.

In the 5-fold cross validation, a training set is first partitioned into 5 segments in a non-overlapping manner, and when one segment is set as a validation set, the remaining 4 segments are set as a training set and used as training data. In this case, the 5-fold cross validation process may be repeated 5 times such that each of the 5 segments may be used once as a validation set. Accuracy of the 5-fold cross validation is calculated as an average of accuracies over 5 iterations. To reduce variability, cross validation may be performed multiple times, and results of the cross validation may be averaged.

Thus, a diagnostic system of the disclosure may perform 5-fold cross-validation multiple times. Subsequently, the 5-fold cross-validation may be calculated by averaging accuracies over each iteration.

FIG. 10 illustrates the performance of an AI model trained by performing 5-fold cross validation on a training set and a test set, respectively, according to an embodiment of the disclosure.

As a result of performing training and validation of the AI model, 28 pieces of feature information (including morphological information and clinical information) may each have different feature importance for predicting FFR. For example, an involved segment showed a highest importance, and body surface area, distal lumen diameter, and minimal lumen diameter within the ROI (MLD), total length of the segment with lumen diameter less than 2 mm (Length-D<2.0 mm), and mean lumen diameter within the worst segment showed a high importance in the stated order.

According to an embodiment of the disclosure, the AI model may select 12 pieces of feature information showing high importance from among the 28 pieces of feature information for training and validation. As a result of the training and validation, as seen on FIG. 10, an AUC when using the 12 pieces of feature information may be higher than an AUC when using the 28 pieces of feature information.

Figure 11:
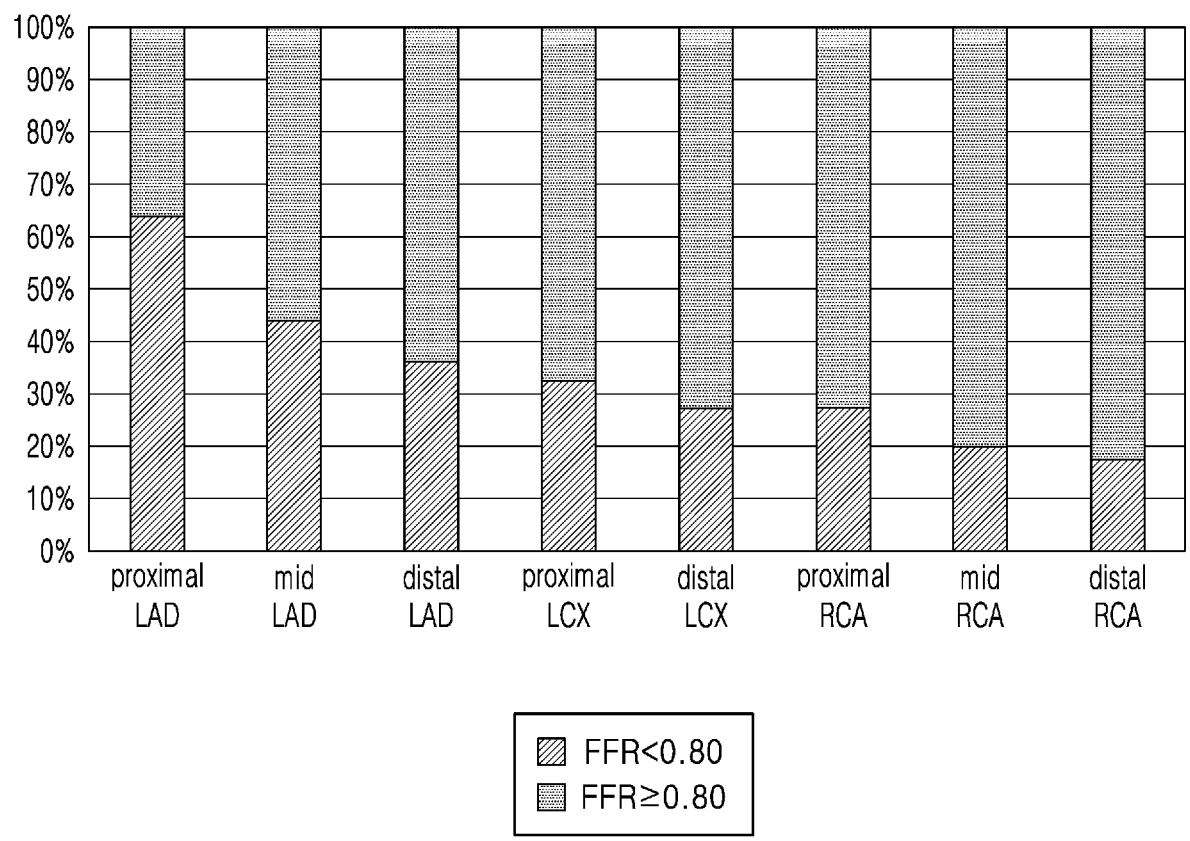
FIG. 11 is a graph illustrating the frequency of FFR of less than 0.80 for each sub-segment in an involved segment, according to an embodiment of the disclosure.

FIG. 11 is a graph illustrating frequency of FFR of less than 0.80 for each sub-segment in an involved segment, according to an embodiment of the disclosure.

Referring to FIG. 11, the frequency of an FFR of less than 0.80 was highest in proximal LAD by being greater than 60% and lowest in distal RCA by being less than 20%.

According to an embodiment of the disclosure, an AI model may assign a priority for detecting a visually estimated lesion considering the frequency of FFR<0.80 for each sub-segment in the involved segment. According to the disclosure, it is possible to quickly identify a lesion and determine a lumen diameter by performing lesion detection in order of priority of lesion classification.

Figure 12:
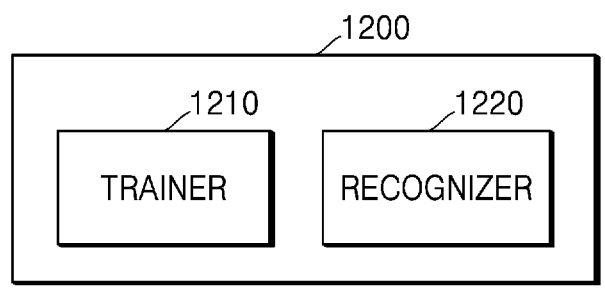
FIG. 12 is a block diagram illustrating a trainer and a recognizer according to various embodiments of the disclosure.

FIG. 12 is a block diagram illustrating a trainer and a recognizer according to various embodiments of the disclosure.

Referring to FIG. 12, a processor 1200 may include at least one of a trainer 1210 and a recognizer 1220. The processor 1200 of FIG. 12 may correspond to the processor 150 of the ischemic lesion diagnostic device 100 of FIG. 2 or a processor (not shown) of the server 200 of FIG. 1.

The trainer 1210 may generate or train a recognition model having criteria for determining a situation. The trainer 1210 may generate a recognition model having criteria for determination by using collected training data.

For example, the trainer 1210 may generate, train, or refine an object recognition model, having criteria for determining FFR according to morphological features of a vessel lumen in a coronary angiography image, by using various coronary angiography images as training data.

As another example, the trainer 1210 may generate, train, or refine a model having criteria for determining an FFR value for an input feature by using various morphological features, clinical features, and FFR value information included in a coronary angiography image as training data.

The recognizer 1220 may estimate target data by using preset data as input data for the trained recognition model.

For example, the recognizer 1220 may obtain (or estimate or infer) a mask image from which a vessel lumen included in a coronary angiography image is separated by using various coronary angiography images as input data for the trained recognition model.

As another example, the recognizer 1220 may estimate (or determine or infer) an FFR value by applying various coronary artery morphological features and clinical features to the trained recognition model. In this case, a plurality of FFR values may be obtained according to a priority.

At least a portion of the trainer 1210 and at least a portion of the recognizer 1220 may be implemented as a software module or manufactured in the form of at least one hardware chip and mounted in an electronic device. For example, at least one of the trainer 1210 and the recognizer 1220 may be manufactured in the form of a dedicated AI hardware chip or as part of an existing general-purpose processor (e.g., a CPU or AP) or a dedicated graphics processor (e.g., a GPU) and may be mounted in various electronic devices or object recognition devices as described above. In this case, the dedicated AI hardware chip is a dedicated processor specialized in probability computation and may quickly process computational tasks in the field of AI such as machine learning due to its higher parallel processing performance than existing general-purpose processors.

When the trainer 1210 and the recognizer 1220 are implemented as a software module (or a program module including an instruction), the software module may be stored in non-transitory computer-readable recording media. In this case, the software module may be provided by an OS or application. Alternatively, some of the software module may be provided by the OS while the rest thereof may be provided by the application.

In this case, the trainer 1210 and the recognizer 1220 may be mounted in a single electronic device, or may be respectively mounted in separate electronic devices. For example, one of the trainer 1210 and the recognizer 1220 may be included in the ischemic lesion diagnostic device 100, and the other one may be included in the server 200. Furthermore, the trainer 1210 and the recognizer 1220 may be connected to each other via a wire or wirelessly such that model information generated by the trainer 1210 may be provided to the recognizer 1220 and data input to the recognizer 1220 may be provided to the trainer 1210 as additional training data.

Furthermore, the above-described methods according to various embodiments of the disclosure may be implemented as an application installable in an existing electronic device.

In addition, embodiments of the disclosure described above may be implemented as a software program including instructions stored in a recording medium that is readable by a computer or a similar device using software, hardware, or a combination thereof. In some cases, the embodiments described herein may be implemented as the processor itself. According to the software implementation, embodiments such as procedures and functions described in the present specification may be implemented as separate software modules. Each of the software modules may perform one or more functions and operations described herein.

A recording medium that may be readable by a device may be provided in the form of a non-transitory computer-readable recording medium. In this regard, the term 'non-transitory' only means that the recording medium does not include a signal and is tangible, and the term does not distinguish between data that is semi-permanently stored and data that is temporarily stored in the recording medium. The non-transitory computer-readable recording medium refers to a medium that stores data semi-permanently and is readable by a device and not a medium storing data for a short time, such as a register, a cache, a memory, etc. Examples of the non-transitory computer-readable recording medium may include a CD, a digital versatile disk (DVD), a hard disk, a Blu-ray disk, a USB, a memory card, ROM, etc.

According to an embodiment of the disclosure, a diagnostic system of the disclosure may predict the presence of ischemia with a high accuracy of about 82%.

Furthermore, according to the disclosure, it is possible to diagnose a hemodynamically significant ischemic condition only with an angiocardiographic image without using an FFR pressure wire, thereby reducing time and cost.

Furthermore, according to the disclosure, it is possible to quickly and accurately predict FFR with a 2D angiocardiographic view image by using AI and make decisions with respect to whether treatment is necessary via diagnosis of ischemia during a procedure, thereby reducing abuse of unnecessary stent procedure.

Despite these effects, the scope of the disclosure is not limited thereby.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A deep learning-based diagnostic method of a device for diagnosing an ischemic lesion in a blood vessel, comprising:
   obtaining an angiography image of a patient's blood vessel;
   extracting a region of interest (ROI) from the angiography image;
   acquiring diameter information of the blood vessel in the ROI;
   extracting morphological features of the blood vessel based on the diameter information; and obtaining a predictive fractional flow reserve (FFR) value by inputting the morphological features to an artificial intelligence (AI) model and determining whether a lesion is an ischemic lesion, wherein the extracting of the ROI comprises:

subdividing a region of the blood vessel of the angiography image into sub-segments, wherein the sub-segments include a proximal reference, a lesion region, and a distal reference of each of a left anterior descending artery (LAD) and a right coronary artery (RCA), a proximal reference, and a distal reference of a left circumflex artery (LCX), assigning a priority to each of the sub-segments of the region of the blood vessel based on a frequency of an FFR <0.80 for each of the sub-segments, detecting a visually estimated lesion from the sub-segments of the region of the blood vessel in an order of priority, and extracting the ROI from the region of the blood vessel based on a location of the visually estimated lesion in the blood vessel, wherein the ROI is a region of the blood vessel from an ostium that is an entrance to the blood vessel to a distal reference that is a preset distance from a lesion included in the blood vessel.

2. The deep learning-based diagnostic method of claim 1, further comprising obtaining clinical features of the patient, wherein the determining of whether the lesion is an ischemic lesion comprises obtaining the predictive FFR value by inputting the morphological features and the clinical features to the AI model and determining whether the lesion is an ischemic lesion.

3. The deep learning-based diagnostic method of claim 1, wherein the acquiring of the diameter information comprises:

obtaining a centerline of the blood vessel included in the ROI; and acquiring the diameter information based on a virtual line perpendicular to the centerline.

4. A non-transitory computer-readable recording medium in which a program executable by a processor is recorded to cause the processor to:

obtain an angiography image of a patient's blood vessel;

extract a region of interest (ROI) from the angiography image;

acquire diameter information of the blood vessel in the ROI;

extract morphological features of the blood vessel based on the diameter information; and obtain a predictive fractional flow reserve (FFR) value by inputting the morphological features to an artificial intelligence (AI) model and determine whether a lesion is an ischemic lesion, wherein to extract of the ROI, the non-transitory computer readable recording medium further causes the processor to:

subdivide a region of the blood vessel of the angiography image into sub-segments, wherein the sub-segments include a proximal reference, a lesion region, and a distal reference of each of a left anterior descending artery (LAD) and a right coronary artery (RCA), a proximal reference, and a distal reference of a left circumflex artery (LCX), assign a priority to each of the sub-segments of the region of the blood vessel based on a frequency of an FFR <0.80 for each of the sub-segments, detect a visually estimated lesion from the sub-segments of the region of the blood vessel in an order of priority, and extract the ROI from the region of the blood vessel based on a location of the visually estimated lesion in the blood vessel, wherein the ROI is a region of the blood vessel from an ostium that is an entrance to the blood vessel to a distal reference that is a preset distance from a lesion included in the blood vessel.

5. A device for diagnosing an ischemic lesion in a blood vessel, the device comprising a processor configured to:

obtain an angiography image of a patient's blood vessel;

extract a region of interest (ROI) from the angiography image;

acquire diameter information of the blood vessel in the ROI;

extract morphological features of the blood vessel based on the diameter information; and obtain a predictive fractional flow reserve (FFR) value by inputting the morphological features to an artificial intelligence (AI) model and determine whether a lesion is an ischemic lesion, wherein, to extract the ROI, the processor is further configured to:

subdivide a region of the blood vessel of the angiography image into sub-segments, wherein sub-segments include a proximal reference, a lesion region, and a distal reference of each of a left anterior descending artery (LAD) and a right coronary artery (RCA), a proximal reference, and a distal reference of a left circumflex artery (LCX), assign a priority to each of the sub-segments of the region of the blood vessel based on a frequency of an FFR <0.80 for each of the sub-segments, detect a visually estimated lesion from the sub-segments of the region of the blood vessel in an order of priority, and extract the ROI from the region of the blood vessel based on a location of the visually estimated lesion in the blood vessel, wherein the ROI is a region of the blood vessel from an ostium that is an entrance to the blood vessel to a distal reference that is a preset distance from a lesion included in the blood vessel.

* * * * *